(12) United States Patent
Goebel (10) Patent No.: US 8,574,562 B2
(45) Date of Patent: Nov. 5, 2013

(54) MICROEMULSION PHARMACEUTICAL COMPOSITION COMPRISING A MACROLIDE IMMUNOSUPPRESSANT DRUG

(75) Inventor: Alexandra Sabine Baerbel Goebel, Halle (DE)

(73) Assignee: Novaliq GmbH, Heidelberg (DE)

( * ) Notice: Subject to any disclaimer, the term of this patent is extended or adjusted under 35 U.S.C. 154(b) by 0 days.

(21) Appl. No.: 13/498,182

(22) PCT Filed: Oct. 7, 2010

(86) PCT No.: PCT/EP2010/064965
§ 371 (c)(1),
(2), (4) Date: Mar. 26, 2012

(87) PCT Pub. No.: WO2011/042485
PCT Pub. Date: Apr. 14, 2011

(65) Prior Publication Data
US 2012/0184511 A1    Jul. 19, 2012

(30) Foreign Application Priority Data
Oct. 8, 2009 (EP) .................................. 09012724

(51) Int. Cl.
*A61K 31/74* (2006.01)

(52) U.S. Cl.
USPC ........................................................ 424/78.05

(58) Field of Classification Search
None
See application file for complete search history.

(56) References Cited

U.S. PATENT DOCUMENTS

| | | |
|---|---|---|
| 2003/0059470 A1 | 3/2003 | Muller |
| 2003/0143250 A1 | 7/2003 | Hauer et al. |
| 2009/0074786 A1 | 3/2009 | Dor |

FOREIGN PATENT DOCUMENTS

| | | |
|---|---|---|
| EP | 1 929 996 A2 | 6/2008 |
| GB | 2 315 216 A | 1/1998 |
| WO | WO 03 053405 A1 | 7/2003 |
| WO | WO 2006 062334 A1 | 6/2006 |
| WO | WO 2006 123354 A2 | 11/2006 |

*Primary Examiner* — Carlos Azpuru
(74) *Attorney, Agent, or Firm* — Dennemeyer & Assoc. LLC.

(57) ABSTRACT

The invention provides novel pharmaceutical compositions of macrolide immunosuppressants. The compositions comprise a hydrophilic component, a lipophilic component, and an amphiphilic component. Preferably, the compositions are formulated as liquid microemulsion. Furthermore, the invention provides uses of such compositions, such as for the topical treatment of inflammatory and autoimmune diseases. Methods for preparing the compositions are also provided.

12 Claims, 4 Drawing Sheets

MICROEMULSION PHARMACEUTICAL COMPOSITION COMPRISING A MACROLIDE IMMUNOSUPPRESSANT DRUG

BACKGROUND

The present invention relates to novel pharmaceutical compositions of macrolide immunosuppressants such as tacrolimus. It further relates to pharmaceutical compositions which are capable of solubilising poorly soluble macrolide immunosuppressants, and which are suitable for topical administration. In further aspects, the invention relates to the therapeutic uses of such compositions.

Immunosuppressants are pharmaceutical compounds that reduce the activity of the immune system. They are commonly used in the therapy of autoimmune diseases and in the prophylaxis and treatment of organ transplants. Autoimmune diseases are conditions which are believed to involve some type of hypersensitivity of the immune system, which is today, for example, known for Crohn's disease, multiple sclerosis, rheumatoid arthritis, ulcerative colitis, Addison's disease and numerous other conditions. After an organ transplantation, the immune system of the recipient nearly always identifies the new organ as foreign and potentially hostile material due to differences in human leukocyte antigen haplotypes between the donor and recipient, and attempts to remove it by attacking and destroying its cellular components.

The immunosuppressants that have been developed for therapeutic use may be classified according to their chemical structure and/or their mechanism of action. Among the early immunosuppressants were in particular antimetabolites, such as azathioprine (a purine synthesis inhibitor) and methotrexate (an antifolate). Substantial therapeutic benefit for transplant recipients was brought about by the advent of the first macrolides, in particular ciclosporin, and later tacrolimus. Further immunosuppressive compounds with related structure and activity include pimecrolimus, everolimus, sirolimus, deforolimus, everolimus, temsirolimus, and zotarolimus. More recently, antibodies and fusion proteins against various cellular and non-cellular targets that are involved in immune responses, such as infliximab, etanercept, rituximab, tocilizumab, and abatacept, have been developed and introduced to the drug market.

Macrolide immunosuppressants such as tacrolimus, sirolimus, everolimus and the like, while being highly active once they are absorbed into the organism or target tissue, are challenging compounds to formulate and deliver to the site of action, in particular due to their poor solubility and relatively large molecular size. For systemic therapy via the oral or intravenous routes of administration, they are typically presented as solubilised formulations comprising substantial amounts of solubilising excipients, such as surfactants and organic solvents.

Tacrolimus, a compound of particular interest in the context of the present invention, was first developed as a concentrate for intravenous infusion after dilution, and as an oral hard capsule formulation. In the concentrate for infusion (currently marketed by Astellas as e.g. Prograf®), tacrolimus (5 mg) is solubilised in a mixture of ethanol (638 mg) and macrogolglycerolricinoleate (200 mg), which excipients are not well tolerated by many patients, but are still considered necessary in view of the very poor solubility of the drug substance. These systemic formulations are used for the prophylaxis and treatment of organ transplant rejection, most frequently with patients that have received a kidney, liver or heart transplant.

More recently, tacrolimus has been developed as an ointment for the treatment of atopic dermatitis. The formulation that is currently marketed (e.g. in Germany since 2002 by Astellas as Protopic®) is available in two strengths (0.3 mg/g and 1 mg/g, respectively), and contains the excipients vaseline, liquid paraffin, solid paraffin, wax, and propylene carbonate.

The therapeutic effectiveness of tacrolimus in the treatment of atopic dermatitis was demonstrated in various placebo-controlled multicentric clinical studies with adult patients in the USA and Europe (1, 4), as well as with children of 3 to 6 years (23, 25). Topical tacrolimus also appears to be effective in the treatment of contact dermatitis (15, 16). In contrast, the experimental use of topical tacrolimus for psoriasis treatment has generally not been successful, even though psoriasis has been clearly identified as an autoimmune disease, possibly due to the thickness and structure of the psoriasis plaques which may represent considerable diffusion barriers for the penetration and uptake of the active ingredient (11, 30). Only in some special cases, relatively positive results were obtained, e.g. by applying occlusive conditions (22), using a liposomal formulation (8), or by treating the relatively thin facial skin or administering the medicine into wrinkles (10, 14, 17, 18, 26, 28, 29).

It is noted, however, that such special cases are associated with a number of drawbacks. For example, skin occlusion is not only considered as unpleasant by the patients, but also poorly feasible for certain areas of the skin (e.g. the face, in folds, near joints etc.), and generally unacceptable in the case of large or multiple affected sites. Liposomal formulations are disadvantageous in that they are not easily manufactured in a reproducible manner at an industrial scale. Moreover, they are difficult to sterilise or produce under aseptic conditions, which could be desirable as the product is not used on intact skin but on adversely affected skin. Treating only certain sites of the affected skin is obviously associated with the disadvantage that other affected sites remain untreated or poorly treated.

The limited effectiveness of conventional ointment formulations of tacrolimus is also indicated by the fact that the currently available topical tacrolimus product (Protopic®) is only approved for the treatment of atopic dermatitis, not of psoriasis.

Other macrolide immunosuppressants are, like tacrolimus, poorly soluble and relatively large molecules which are also difficult to formulate and which are likely to possess the same limitations with respect to penetrating psoriasis plaques. None of these compounds have been successfully developed as topical formulations for psoriasis treatment.

Consequently, there is a need for improved topical formulations of macrolide immunosuppressive compounds such as tacrolimus which are suitable for, and effective in, the treatment of other conditions than atopic dermatitis. In particular, there is a need for topical medicines for treating psoriasis, using formulations which do not require occlusion, incorporate liposomes, which are easily manufactured at large scale, and/or which do not possess one or more of the disadvantages of the compositions that are known today.

It is an object of the present invention to provide such compositions. Further objects are to provide beneficial uses of compositions of macrolide immunosuppressive compounds and methods for preparing such compositions. Still further objects will be understood in the light of the description and the patent claims.

It is noted that WO 03/053405 A1 discloses emulsions for ophthalmic use and proposed for the treatment of dry eye syndrome. The emulsions have a droplet size of 150 nm to 250 nm (p. 7, line 13) and are therefore conventional emulsions which, in contrast to microemulsions, do not form spontaneously, and are thermodynamically unstable and optically anisotropic. Moreover, the emulsions comprise more than 90% water and a cationic surfactant. There is no hint that these compositions could be useful for administration to the skin.

EP 1 929 996 A2 also describes o/w-type emulsions for ophthalmic use. The emulsions have a preferred particle size of 100 nm to 250 nm (p. 4, paragraph [0038]) and are prepared by conventional emulsification techniques requiring the input of energy (p. 5, paragraph [0043]), which lead to convention emulsions which are, in contrast to microemulsions, thermodynamically unstable and optically anisotropic. The document does not disclose the use of the emulsions for treating the skin.

WO 2006/062334 A1 discloses so-called microemulsion pre-concentrates (also known as self-microemulsifying drug delivery systems or SMEDDS) which, upon the addition of an aqueous phase, spontaneously form microemulsions. The pre-concentrates are filled e.g. into capsules and are for oral administration. The inventors of the pre-concentrates had found that the compositions lead to higher systemic bioavailability of tacrolimus after oral ingestions.

US 2003/0143250 A1 describes microemulsion pre-concentrates comprising the active ingredient, ciclosporin, which achieve a high systemic bioavailability and low inter-subject variability of the incorporated drug after oral administration (p. 18, paragraphs [0257] to [0259]. The document does not disclose other drugs that ciclosporin.

GB 2 315 216 A relates to self-microemulsifying and microemulsion composition of tacrolimus for oral administration. Again, the compositions achieve improved pleasma levels of the incorporated drug substance. The document does not teach other uses than oral administration.

US 2003/0059470 A1 teaches o/w-emulsions that are prepared by conventional processes and have droplet sizes in a range of 100 nm up to 10 µm, preferably of 200 nm to 500 nm, and are thus thermodynamically unstable and optically anisotropic (p. 5, paragraph [0075]).

WO 2006/123354 A2 provides water-free self-microemulsifying compositions (or microemulsion pre-concentrates, or SMEDDS) of hydrophobic drugs for oral use which may form microemulsions upon addition of an aqueous phase. The document does not teach other uses than oral administration.

SUMMARY OF THE INVENTION

The present invention provides a pharmaceutical composition comprising a therapeutically active ingredient selected from the group of macrolide immunosuppressants, a hydrophilic component, a lipophilic component, and an amphiphilic component. The composition is further characterised in that it is formulated as a microemulsion.

In a particularly useful embodiment, the invention provides a liquid microemulsion comprising tacrolimus as the active ingredient. The constituents of the hydrophilic, lipophilic and amphiphilic components are preferably selected from excipients that are well tolerated by the skin and/or mucosa. In particular, it is preferred that the tacrolimus microemulsion comprises water.

The hydrophilic component may comprise water in combination with one or more liquid glycols, such as glycerol, propylene glycol, pentylene glycol, and/or polyethylene glycol. The lipophilic component may be composed of one or more oily excipients used in cosmetic or dermatological preparations, such as isopropyl myristate, isopropyl palmitate, dibutyl adipate, diisopropyl adipate, and/or triglycerides. The amphiphilic component typically comprises one or more surfactants, such as phospholipids, alkyl polyglucosides, sorbitan esters with fatty acids, and/or pegylated mono- and diesters of glycerol with fatty acids.

The invention further provides the use of microemulsion compositions comprising a macrolide immunosuppressant for topical treatments, such as for administration to the skin, a mucosa, or an eye. Moreover, it provides the use of such compositions for the treatment of diseases and conditions such as atopic dermatitis, psoriasis, collagenosis, inflammatory diseases of the bowel, inflammatory diseases of the eye, or transplant rejection.

In yet a further aspect, the invention provides a method for preparing such compositions. The method is characterised in that the ingredients of a composition are combined and mixed without applying high shear conditions or pressure homogenisation.

DETAILED DESCRIPTION OF THE INVENTION

According to the present invention, pharmaceutical compositions are provided which comprise a therapeutically active ingredient selected from the group of macrolide immunosuppressants, a hydrophilic component, a lipophilic component, and an amphiphilic component. The composition is further characterised in that it is formulated as a microemulsion.

As used herein, a pharmaceutical composition means a composition comprising at least one pharmaceutically active compound and at least one excipient, wherein the composition is formulated and processed in such a way that it is suitable for administration to a human or animal. In the case of the present invention, the active ingredient is a macrolide immunosuppressant, i. e. a compound which suppresses the activity of the immune system or at least one component thereof, and which comprises a macrolide ring structure, which is typically defined as a relatively large macrocyclic lactone ring (e.g. from 14-16 members in the case of macrolide antibiotics and often more than 20 ring members in the case of macrolide immunosuppressants which are of interest here) to which one or more deoxy sugar residues may be attached.

Macrolide immunosuppressants which are useful for carrying out the invention include sirolimus, everolimus, tacrolimus, pimecrolimus, ridaforolimus, temsirolimus, and zotarolimus. Particularly preferred are pimecrolimus, sirolimus, everolimus, and tacrolimus. As used herein, these nonproprietary names are understood so as to include any salts, solvates, isomers, conjugates or other closely related derivatives of the respective active principles. In one of the specific embodiments, the active ingredient is tacrolimus monohydrate (hereinafter also referred to as "tacrolimus").

Tacrolimus ($C_{44}H_{69}NO_{12}*H_2O$, MW 822.05) is a macrolide lactone with a melting point of 127-129° C. It exhibits two $pk_s$ values of 9.97±0.7 and −2.38±0.7, respectively. Its water solubility is very poor over the pH range of 1 to 10, and only above pH 10 it increases about twofold (24). It is soluble in methanol, ethanol, acetone, chloroform, ethyl acetate, and diethyl ether (20). Its high lipophilicity is also reflected by its partition coefficient, log $P_{octanol/buffer}$, of 3.96±0.83 (24).

Tacrolimus was first isolated from the bacterium *Streptomyces tsukubaensis* in 1984 in Japan. The name tacrolimus stems from its place of discovery, Tsukuba, its chemical core structure, i.e. macrolide, and its activity as immunosuppressant. Its immunosuppressive activity in vitro is 50-100 times, and in vivo 10-20 times, higher than that of ciclosporin (12).

Even though tacrolimus and ciclosporin are chemically not very closely related, it appears that their mechanisms of action are the same or at least very similar. Generally speaking, they block the release of interleukin-1 from macrophages and interleukin-2 from T-helper cells via inhibition of the transcription process at the genes that code for the respective cytokines.

The content of the active compound in the composition of the invention is generally selected with an eye on the solubility of the compound in the excipients mixture, or carrier, and on the desired product application, taking e.g. into account the volume of the formulation which should be administered, which may be restricted by the nature of the site of administration (e.g. the eye). In the case of tacrolimus, the content or concentration in the composition will generally be in the range from about 0.00001 to about 20 wt.-%. More preferably, it is selected in the range from about 0.01 to 1 wt.-%. In particular embodiments, the composition comprises about 0.03 wt.-%, 0.05 wt.-%, 0.1 wt.-%, 0.3 wt.-%, 0.5 wt-% and 1.0 wt.-%, respectively.

The composition of the invention is further characterised in that it is a microemulsion. As used herein, a microemulsion is a clear, thermodynamically stable, optically isotropic mixture of a lipophilic component, a hydrophilic component, and an amphiphilic component. Typically, a microemulsion forms spontaneously when the components are combined and mixed with each other, without requiring high energy input as is normally required for the formation of an "ordinary" emulsion. Microemulsions may have a colloidal lipophilic phase dispersed in a hydrophilic phase, or a hydrophilic phase colloidally dispersed in a lipophilic phase. The size of the dispersed phases is usually in the range from about 5 nm to about 400 nm, and most often below about 200 nm. In one of the preferred embodiments of the invention, the particle size is from about 5 nm to about 100 nm.

In terms of its rheological properties, the microemulsion may be in the form of a liquid or a gel, i.e. in liquid or semisolid form. In a preferred embodiment, the microemulsion is in liquid form.

The composition is further characterised in that it comprises a hydrophilic component. As used herein, a component is a pharmaceutically acceptable excipient or mixture of excipients, and hydrophilic means in the present context that the component is miscible with water, or at least substantially soluble in water. Most preferably, the hydrophilic component is liquid. For example, the hydrophilic component may be composed of water itself (including predominantly aqueous solutions such as buffers etc.), liquid polar solvents, or mixture of water and one or more of such polar solvents. Useful polar solvents include, for example, alcohols such as ethanol and liquid glycols. Particularly preferred glycols include glycerol, propylene glycol, liquid polyethylene glycols, and 1,2-pentane diol (herein also referred to as pentylene glycol).

Diols such as propylene glycol and pentylene glycol are particularly preferred agents in this context as they exhibit several beneficial effects. Apart from serving as constituents of the hydrophilic component, they are very well tolerated by the skin. Moreover, they possess a small relatively lipophilic molecular region by virtue of which they may also be considered as somewhat amphiphilic, thus enforcing the functionality of the amphiphilic component of the composition and enhance the solubilisation of poorly water-soluble ingredients. They have high affinity to the skin and hair. Furthermore, they exhibit substantial antimicrobial properties so that they allow for the formulation of aqueous topical compositions without any further preservatives, or with reduced preservative levels.

Furthermore, preferred hydrophilic components include mixtures of (a) water and (b) a liquid glycol, such as water and propylene glycol or water and pentylene glycol. For such mixtures, the ratio of water to glycol (or glycols) may be freely selected. More preferably, the ratio is in the range from about 1:10 to about 10:1. In further embodiments, the ratio is in the range from 1:3 to 3:1, or from 1:2 to 2:1, respectively. Examples of useful hydrophilic components include water and pentylene glycol (2:1), water and propylene glycol (1:2).

As mentioned, the hydrophilic component may comprise water. The water content is preferably at least about 5 wt.-%, relative to the weight of the total composition. While water-free microemulsions and self-microemulsifying compositions of certain active pharmaceutical ingredients have been described in prior art, these are difficult to envision for topical administration. For example, the limited amounts of water present in the skin or a mucosa will not normally achieve a conversion of a self-microemulsifying composition into a microemulsion. In any case, the inventors have found that the invention is particularly useful for the topical administration of a macrolide immunosuppressant when the hydrophilic component comprises water itself, such as at least about 5 wt.-% of water, relative to the total composition, or even at least 10 wt.-%, or at least 20 wt.-%, respectively. In fact, formulations exhibiting excellent properties (such as good skin permeation and local tolerability) may contain as much as 40 wt.-%, 45 wt.-%, 50 wt.-% or more water. Consequently, the hydrophilic component of the composition may represent a substantial weight fraction of the total composition, such as at least about 20 wt.-%, or even in the range from about 50 to about 80 wt.-%.

Another essential component of the composition is a lipophilic component. In the microemulsion, the lipophilic component will substantially contribute to the formation of a colloidally dispersed lipophilic phase. The lipophilic component may be composed of any suitable, pharmaceutically acceptable lipophilic excipient or mixture of excipients which are capable of forming the lipophilic phase. Preferred excipients that can be used alone or in combination with each other as the lipophilic component include oily compounds that are well tolerated by the skin and/or mucosae, such as triglyceride oils, liquid paraffins, liquid waxes, and in particular the compounds isopropyl myristate, isopropyl palmitate, dibutyl adipate, and diisobutyl adipate.

Preferably, the lipophilic component is selected to yield a dispersed lipophilic phase in the microemulsion, so that the composition is in the form of a o/w-microemulsion. The particle size of the dispersed lipophilic phase in the microemulsion is preferably in the range of 5 to 200 nm, and in particular in the rage from 5 to 100 nm.

It is also preferred that the content of the lipophilic component is kept at or below about 50 wt.-% relative to the total composition in order to allow for a high content of the hydrophilic component. In further embodiments, the lipophilic component is present at an amount of not more than about 30 wt-%, or not more than about 20 wt.-%, respectively. On the other hand, the amount of lipophilic phase should be high enough to solubilise much or all of the active ingredient. In the case of tacrolimus, for example, a stable microemulsion composition comprising 0.1% of active ingredient and a significant amount of hydrophilic component (e.g., 50-80 wt.-%) including water can be formulated with e.g. 10 wt.-% of a lipophilic component consisting of dibutyl adipate.

According to the invention, the composition comprises an amphiphilic component as a further essential feature. In fact, the presence of an amphiphilic component is an essential requirement for the formation of a microemulsion. The amphiphilic component comprises at least one, and optionally at least two amphiphilic excipients, e.g. surfactants. In a preferred embodiment, a combination of two or more surfactants is present in the amphiphilic component.

It is noted that some of the commonly used surfactants in the pharmaceutical or cosmetic field are in fact mixtures of chemically related molecules. It is also noted that the technical literature relating to microemulsions often refers to surfactants and co-surfactants, even in the absence of functional differences between them, whereas in the context of the present invention surfactants are simply termed as such, without using the term co-surfactant. Surfactants may also be referred to as emulsifiers.

As constituents of the amphiphilic component, any amphiphilic excipient suitable for pharmaceutical use may be selected. Preferably, the amphiphilic component is composed of surfactants that are physiologically well tolerated after administration to the skin and/or a mucosa. For example, the one or more surfactants may be selected from the group of phospholipids, alkyl polyglucosides, sorbitan esters with fatty acids, polyalkyleneglycol ethers of fatty alcohols (e.g. lauryl-, stearyl-, cetyl-, or palmityl alcohol), and/or pegylated mono- and diesters of glycerol with fatty acids. Examples of especially suitable surfactants are lecithins, in particular those which consist predominantly of phospholipids, purified or synthetic phosphatidylcholines, phosphatidylglycerols, sorbitan monooleate, polyoxyethyleneglycol monostearate, polyoxyethyleneglycol ethers of fatty alcoholols such as polyoxyethylene(4)lauryl ether, alkyl (poly)glucosides such as decyl glucoside.

Preferred mixtures of surfactants include (a) lecithin combined with an alkyl polyglucoside, (b) a lecithin combined with sorbitan monooleate, and (c) a lecithin combined with polyoxyethyleneglycol monostearate. Suitable ratios between the first and the second surfactant in binary mixtures are usually in the range from about 1:10 to about 10:1, and preferably in the range from about 3:1 to 1:3.

The amount of amphiphilic component in the microemulsion composition should generally be selected below 65 wt.-%, and more preferably in the range from about 15 to about 35 wt.-%. In fact, one of the particular benefits of the present invention is that poorly soluble macrolides such as tacrolimus can be formulated for topical use in well-tolerated compositions comprising the active ingredient in solubilised form even at a relatively low surfactant content, such as 25 or 30 wt.-%.

In a further aspect, it is preferred that the composition comprises a larger amount of hydrophilic component than of amphiphilic component, i.e. the ratio of hydrophilic to amphiphilic component is preferably 1:1 or higher, such as in the range from about 1:1 to 3:1. It has been found by the inventors that this ratio reconciles the need for solubilising the macrolide immunosuppressant in the microemulsion with the need to provide patients with a formulation which is well tolerated by the skin and the mucosae, and which at the same time is readily taken up by the skin or mucosa without leaving oily residues.

Apart from the components and excipients described as essential for carrying out the invention, the composition may comprise further ingredients as required. For example, it may contain a further active ingredient, e.g. a corticosteroid, an antibiotic, an antimycotic, and/or an antiviral agent. Moreover, it may comprise one or more further excipients, such as agents for adjusting the pH (e.g. acids, buffer salts, bases), antioxidants (e.g. ascorbic acid, vitamin E and its derivatives, BHT, BHA, disodium EDTA, etc.), preservatives (e.g. cationic surfactants such as benzalkonium chloride; benzyl alcohol, sorbic acid etc.), permeation enhancers (DMSO, Transcutol®, menthol, oleic acid, n-alkanols, 1-alkyl-2-pyrrolidones, N,N-dimethlyalkanamides, and 1,2-alkanediols, etc.), and the like.

The composition of the invention, as it is in the form of a microemulsion, is easily manufactured and scaled up into industrial scale production. It is formed as the ingredients are combined and mixed together, even in the absence of high shear conditions or pressure homogenisation. Therefore, the composition may be prepared using any standard mixing equipment which is suitable for the preparation of liquid pharmaceutical formulations at the appropriate scale. Optionally, ultrasound treatment of the combined ingredients may be used to accelerate the formation of a homogeneous microemulsion.

In a further aspect, the invention provides the use of the compositions described above as medicines. Particularly beneficial is the use for topical treatment which also involves topical administration, i.e. administration to the skin or to a mucosa, such as a mucosa of the oral or nasal cavity, of the eye, or of the small or large intestine. In one of the specific embodiments, the composition is used for administration to the skin.

Preferably, the topical use does not involve occlusive conditions. In fact, it was found by the inventor that occlusion is not required for the composition to deliver their active ingredient efficiently into the target layers of the skin, in particular the dermis. This is an important and unexpected benefit of the present invention and potentially enables the treatment of larger skin areas, which patients do not normally tolerate when occlusive conditions are required.

The diseases and conditions in which the therapeutic use of the composition may be beneficial include in particular conditions involving inflammatory and/or autoimmune processes, such as atopic dermatitis, psoriasis, collagenosis, inflammatory diseases of the bowel, inflammatory diseases of the eye, and/or transplant rejection. In contrast to prior art compositions of macrolide suppressants, the compositions have properties which allow the effective treatment of psoriasis, and this therapeutic use constitutes one of the preferred embodiments of the invention. Further potential uses include chronic wounds and burns. As used herein, a therapeutic use is understood as including both curative and prophylactic treatment methods.

Further embodiments will become obvious from the following examples which illustrate the invention in some of its major aspects, without limiting the scope thereof.

EXAMPLES

Example 1

Preparation of Water-Containing Microemulsions with Tacrolimus

Four different microemulsion compositions according to the invention were formulated and prepared by combining and mixing the respective ingredients. The compositions are shown in tables 1 to 7. Transparent or slightly opalescent microemulsions formed spontaneously upon mixing. After three months of storage at room temperature, samples of the three microemulsions were visually inspected. No indication of physical instability was found.

TABLE 1

Composition A

| Component | | wt.-% |
|---|---|---|
| Active ingredient | Tacrolimus | 0.1 |
| Hydrophilic component | Water | 39.9 |
| | Pentylene glycol | 20.0 |
| Lipophilic component | Dibutyl adipate (Cetiol ® B) | 10.0 |
| Amphiphilic component | Lecithin (Phospholipon ® 90G) | 10.0 |
| | Decyl glucoside (Plantacare ® 2000 UP) | 20.0 |
| Other | None | — |
| Total | | 100.0 |

TABLE 2

Composition B

| Component | | wt.-% |
|---|---|---|
| Active ingredient | Tacrolimus | 0.1 |
| Hydrophilic component | Water | 21.63 |
| | Propylene glycol | 43.27 |
| Lipophilic component | Dibutyl adipate (Cetiol ® B) | 10.0 |
| Amphiphilic component | Lecithin (Phospholipon ® 90G) | 6.3 |
| | PEG-20-glycerol monostearate (Tagat ® S2) | 18.8 |
| Other | None | — |
| Total | | 100.0 |

TABLE 3

Composition C

| Component | | wt.-% |
|---|---|---|
| Active ingredient | Tacrolimus | 0.1 |
| Hydrophilic component | Water | 44.9 |
| | Pentylene glycol | 20.0 |
| Lipophilic component | Dibutyl adipate (Cetiol ® B) | 10.0 |
| Amphiphilic component | Lecithin (Phospholipon ® 90G) | 15.0 |
| | Sorbitan monooleate (Span ® 80) | 10.0 |
| Other | None | — |
| Total | | 100.0 |

TABLE 4

Composition D

| Component | | wt.-% |
|---|---|---|
| Active ingredient | Tacrolimus | 0.1 |
| Hydrophilic component | Water | 21.63 |
| | Propylene glycol | 43.27 |
| Lipophilic component | Isopropylmyristate | 10.0 |
| Amphiphilic component | Lecithin (Phospholipon ® 90G) | 6.3 |
| | PEG-20-glycerol monostearate (Tagat ® S2) | 18.8 |
| Other | None | — |
| Total | | 100.0 |

TABLE 5

Composition E

| Component | | [g] |
|---|---|---|
| Active ingredient | Tacrolimus | 0.1 |
| Hydrophilic component | Water | 22.0 |
| | Propylene glycol | 43.2 |
| Lipophilic component | Isopropylmyristate | 10.1 |
| Amphiphilic component | Lecithin (Phospholipon ® 90G) | 6.0 |
| | PEG-20-glycerol monostearate (Tagat ® S2) | 19.0 |
| Other | Tartaric acid 10 wt.-% aqueous solution for adjusting the pH to 4.0 ± 0.2 | q.s. |
| Total | | 100.4 |

TABLE 6

Composition F

| Component | | [g] |
|---|---|---|
| Active ingredient | Tacrolimus | 0.1 |
| Hydrophilic component | Water | 45.0 |
| | Pentylene glycol | 19.9 |
| Lipophilic component | Isopropylmyristate | 10.1 |
| Amphiphilic component | Lecithin (Phospholipon ® 90G) | 15.0 |
| | Sorbitan monooleate (Span ® 80) | 10.0 |
| Other | Tartaric acid 10 wt.-% aqueous solution for adjusting the pH to 4.0 ± 0.2 | q.s. |
| Total | | 100.1 |

TABLE 7

Composition G

| Component | | [g] |
|---|---|---|
| Active ingredient | Tacrolimus | 0.1 |
| Hydrophilic component | Water | 40.1 |
| | Pentylene glycol | 20.1 |
| Lipophilic component | Isopropylmyristate | 10.3 |
| Amphiphilic component | Lecithin (Phospholipon ® 90G) | 10.1 |
| | Polyoxyethylene (4) lauryl ether (Brij ® 30) | 20.0 |
| Other | Tartaric acid 10 wt.-% aqueous solution for adjusting the pH to 4.0 ± 0.2 | q.s. |
| Total | | 100.6 |

Example 2

Skin and Mucosa Toxicity Tests

The three formulations A, B and C prepared according to example 1, but without active ingredient, were tested for their potential to produce toxic tissue effects on skin and mucosae, using the HET CAM ("hen's egg test—chorio allantois membrane") method. This membrane is used 8-10 days after fertilisation when it already possesses a functional vasculature but no nervous tissue. Placebo formulations were used in order to determine the irritation potential of the carrier rather than that of the active ingredient.

The HET CAM model is an internationally accepted alternative to animal models and yields similar results without causing any pain. In the HET CAM model, the presence of irritation is indicated by changes in the vasculature, including a hypervascularised CAM and an increased vascular perfusion (27). Laser doppler flux (LDF) was used to quantify the perfusion after defined time intervals if approx. 30 minutes after applying the formulations, as irritation-induces increases of perfusion can be estimated by the resulting increases in LDF.

For the present experiments, naturally inseminated eggs of New Hampshire hens were used. The eggs were kept for 8 days at 37° C. and 55 r.h. and turned every 12 hours. Thereafter, the eggs were transferred to a laminar flow box for microsurgical manipulation. At the egg pole having the larger radius (i.e. the weaker convexity), a circular opening of 1.5 cm in diameter was cut out of the shell, and the CAM was dissected. On each CAM, 100 µl of the test solution was applied. Phosphate buffer was used as negative control, sodium dodecyl sulphate solution as positive control. The CAM was then illuminated with monochromatic low energy helium-neon laser (632.8 nm). After 30 minutes, the egg underwent LDF testing. In result, none of the formulations exhibited any significant increases in vascular perfusion, but only slight decreases, thus indicating the absence of any potential for irritation.

Example 3

Skin Penetration of Tacrolimus

The three tacrolimus microemulsions A, B, and C prepared according to example 1 were further tested in skin permeation experiments using excised human mamma skin and Franz diffusion cells (Crowne Glass Company, Somerville, N.Y., USA). Phosphate buffer pH 7.4 was used as acceptor fluid. The skin samples were fixed onto a filter using a metal clip. A glass lid was used to cover the Franz cells to avoid evaporation losses during the experiments. Skin from three donors was used in the series of tests.

For each diffusion experiment, approx. 20 µL of the respective microemulsion was applied to the skin specimen. Subsequently, the specimen was placed onto the filter of the Franz cell and fastened. The diffusion cell was kept at 32° C. for 30, 300, or 1,000 minutes. After the testing period, residuals of the microemulsion were removed from the surface of the skin using a swab, and three circular punch biopsies of 6 mm in diameter were punched out from each skin specimen, using a Kromayer die cutter (Stiefel Laboratorium, Offenbach, Germany). The biopsies were then frozen and microtomised. The horizontal slices that were obtained are listed in table 5.

The swabs used for removing microemulsion residues were extracted with methanol (5 mL) for 12 hours. The skin slices were extracted for 1 hour using 0.3 to 0.5 ml of methanol, depending on the expected amount of drug substance. Tacrolimus was then quantified by HPLC with MS-detection using mycophenolate mofetil as internal standard.

TABLE 8

| Skin layer | Microtome slices (thickness) |
| --- | --- |
| Stratum corneum (SC) | 10 µm |
| Live epidermis (EP) | 4 slices of 20 µm |
| Dermis 1 (adjacent to epidermis) (DR1) | 5 slices of 40 µm |
| Dermis 2 (DR2) | 5 slices of 40 µm |
| Dermis 3 (DR3) | 5 slices of 40 µm |
| Dermis 4 (DR4) | 5 slices of 40 µm |
| Dermis 5 (DR5) | 5 slices of 40 µm |

In result, it was found that formulations A and C delivered tacrolimus rapidly and efficiently into the skin, in particular into the dermis which, due to the lymphocytes that reside therein, represents an important target for the active ingredient. The rapid increase in tacrolimus levels after 30 and 300 minutes is more pronounced for these formulations than for formulation B. However, after 1,000 minutes, formulation B has delivered nearly as much tacrolimus as the other two formulations into the dermis, and the amount of drug which is delivered into the acceptor fluid is the highest for all three formulation. Detailed results are depicted in FIGS. 1-7.

Figure 1:
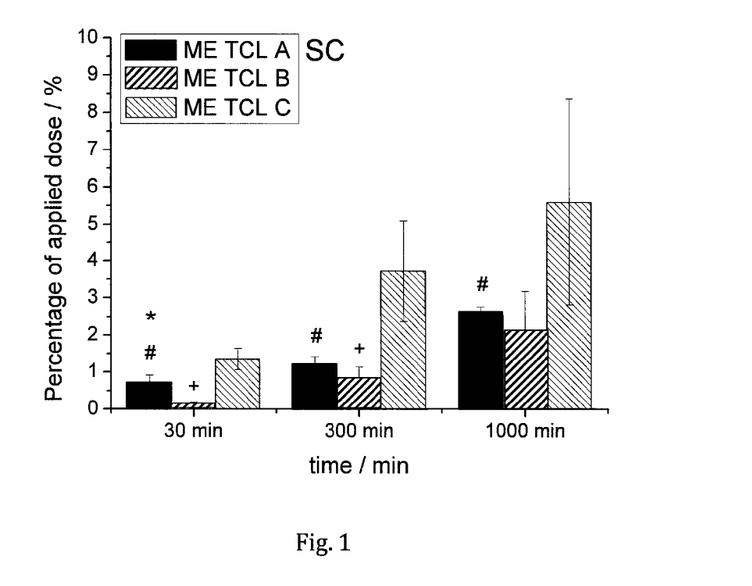
Figure 2:
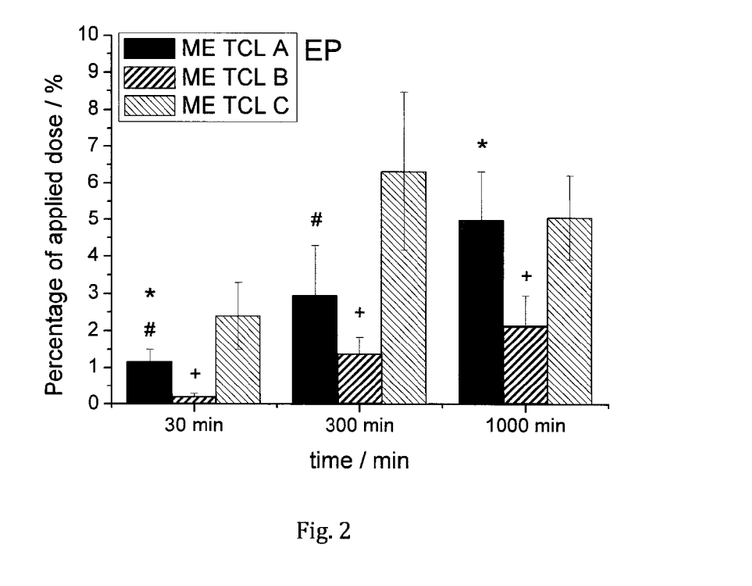
Figure 3:
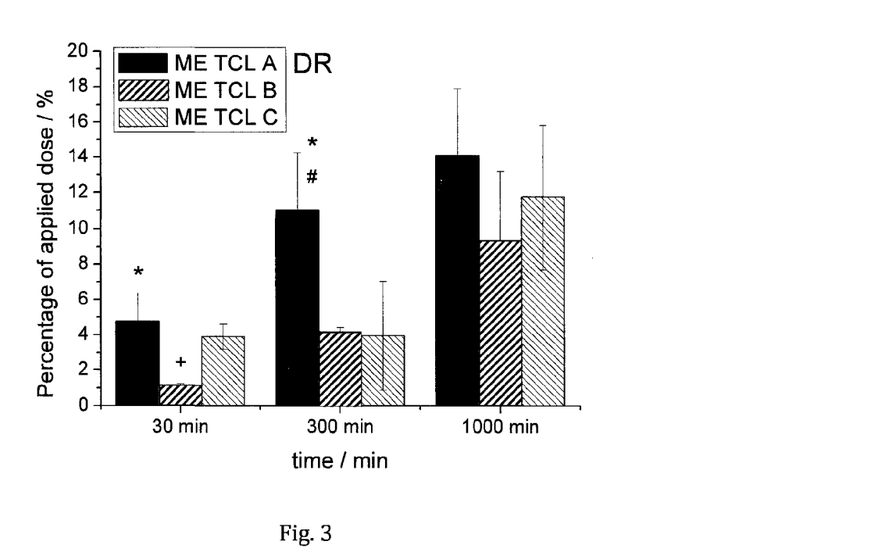
Figure 4:
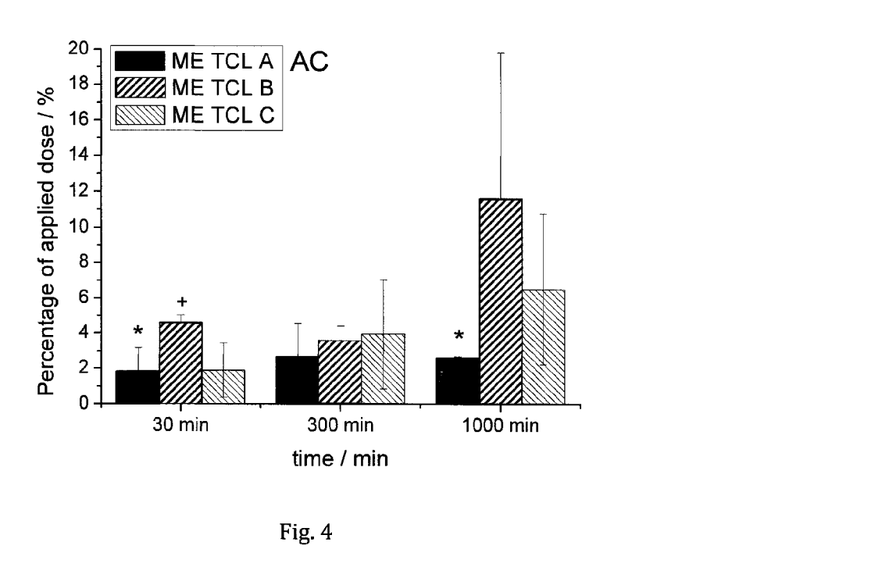

FIGS. 1 to 4 show the tacrolimus dose fractions found in the various skin layers (FIG. 1: stratum corneum; FIG. 2: viable epidermis; FIG. 3: dermis) and the acceptor medium (FIG. 4) 30, 300, and 1,000 minutes after application of formulations A, B and C (here designated as ME TCL A, ME TCL B, and ME TCL C, respectively), relative to the applied dose (n=9; $\bar{x}\pm SD$; *$p<0.01$ ME TCL A versus ME TCL B, #$p<0.01$ ME TCL A versus ME TCL C, +$p<0.01$ ME TCL B versus ME TCL C).

Figure 5:
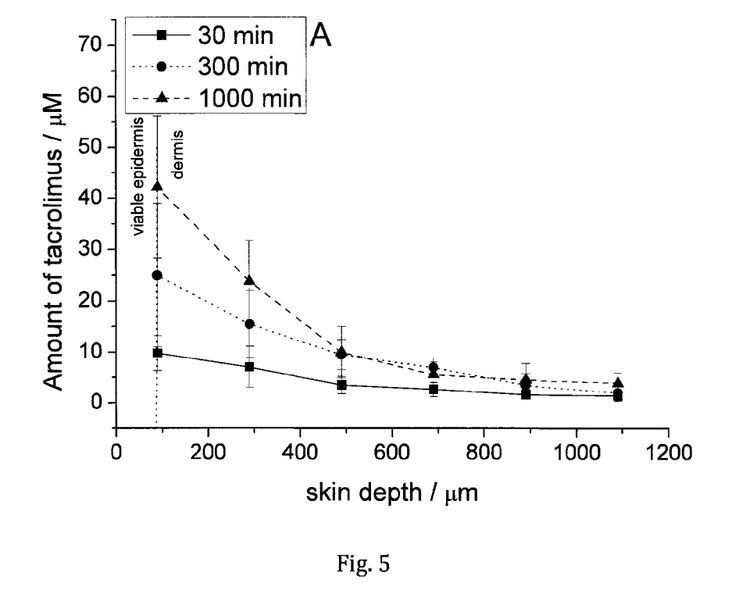
Figure 6:
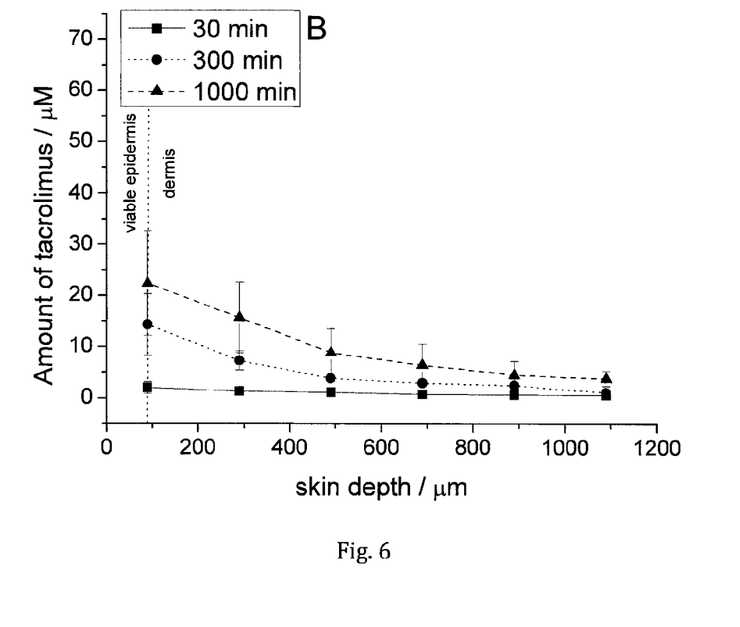
Figure 7:
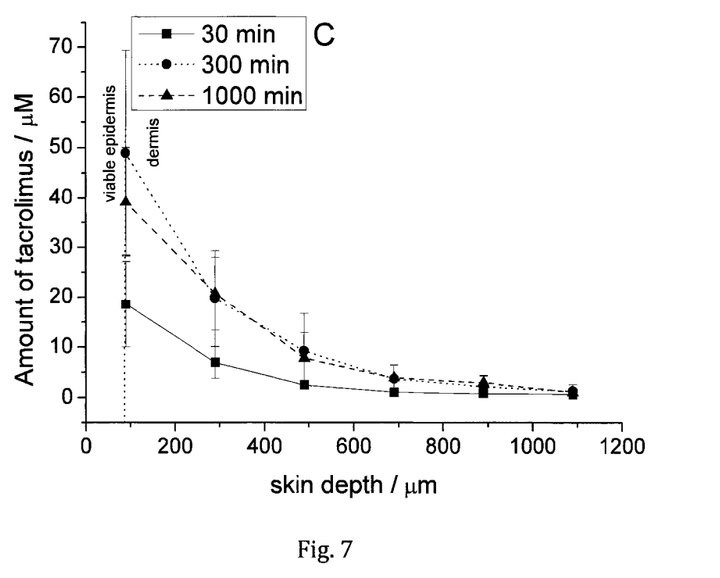

FIGS. 5 to 7 shows the concentration of tacrolimus over the skin depth 30, 300 and 1,000 minutes after application of formulations A (FIG. 5), B (FIG. 6) and C (FIG. 7) (n=9; $\bar{x}\pm SD$; stratum corneum not shown).

In conclusion, all three exemplary formulations demonstrate that the microemulsions according to the invention are capable of delivering macrolide immunosuppressants such as tacrolimus across the major penetration and permeation barrier represented by the stratum corneum. Moreover, they are capable of delivering significant fractions of the administered drug into the skin without requiring occlusion.

LITERATURE REFERENCES

1. Alaiti S, Kang S W, Fiedler V C, et al. Tacrolimus (FK506) ointment for atopic dermatitis: A phase I study in adults and children. Journal of the American Academy of Dermatology 1998; 38.
2. Alany R G, Rades T, Nicoll J, Tucker I G, Davies N M. W/O microemulsions for ocular delivery: Evaluation of ocular irritation and precorneal retention. Journal of Controlled Release 2006; 111.
3. Billich A, Aschauer H, Aszodi A, Stuetz A. Percutaneous absorption of drugs used in atopic eczema: pimecrolimus permeates less through skin than corticosteroids and tacrolimus. International Journal of Pharmaceutics 2004; 269.
4. Boguniewicz M, Fiedler V C, Raimer S, et al. A randomized, vehicle-controlled trial of tacrolimus ointment for treatment of atopic dermatitis in children. Journal of Allergy and Clinical Immunology 1998; 102.
5. Bonina F P, Montenegro L, Scrofani N, et al. Effects of Phospholipid Based Formulations on in-Vitro and in-Vivo Percutaneous-Absorption of Methyl Nicotinate. Journal of Controlled Release 1995; 34.
6. Changez M, Chander J, Dinda A K. Transdermal permeation of tetracaine hydrochloride by lecithin microemulsion: In vivo. Colloids and Surfaces B-Biointerfaces 2006; 48.
7. Changez M, Varshney M, Chander J, Dinda A K. Effect of the composition of lecithin/n-propanol/isopropyl myristate/water microemulsions on barrier properties of mice skin for transdermal permeation of tetracaine hydrochloride: In vitro. Colloids and Surfaces B-Biointerfaces 2006; 50.
8. Erdogan M, Wright J R, McAlister V C. Liposomal tacrolimus lotion as a novel topical agent for treatment of immune-mediated skin disorders: experimental studies in a murine model. British Journal of Dermatology 2002; 146.

9. Franz T J. Percutaneous Absorption—Relevance of Invitro Data. Journal of Investigative Dermatology 1975; 64.
10. Freeman A K, Linowski G J, Brady C, et al. Tacrolimus ointment for the treatment of psoriasis on the face and intertriginous areas. Journal of the American Academy of Dermatology 2003; 48.
11. Gupta A K, Adamiak A, Chow M. Tacrolimus: a review of its use for the management of dermatoses. Journal of the European Academy of Dermatology and Venereology 2002; 16.
12. Honbo T, Kobayashi M, Hane K, Hata T, Ueda Y. The oral dosage form of FK-506. Transplantation Proceedings 1987; 19.
13. Köszegi D, Nothhelfer B, Leimbeck R. Der HET-CAM-Test (Hühner-Ei-Test-Chorioallantoismembran). Euro Cosmetics 6 1999.
14. Kroft E B M, Erceg A, Maimets K, Vissers W, van der Valk P G M, van de Kerkhof P C M. Tacrolimus ointment for the treatment of severe facial plaque psoriasis. Journal of the European Academy of Dermatology and Venereology 2005; 19.
15. Lauerma A I, Maibach H I, Granlund H, Erkko P, Kartamaa M, Stubb S. Inhibition of Contact Allergy Reactions by Topical Fk506. Lancet 1992; 340.
16. Lauerma A I, Stein B D, Homey B, Lee C H, Bloom E, Maibach H I. Topical Fk506—Suppression of Allergic and Irritant Contact-Dermatitis in the Guinea-Pig. Archives of Dermatological Research 1994; 286.
17. Lebwohl M, Freeman A, Chapman M S, Feldman S, Hartle J, Henning A. Proven efficacy of tacrolimus for facial and intertriginous psoriasis. Archives of Dermatology 2005; 141.
18. Lebwohl M, Freeman A K, Chapman M S, et al. Tacrolimus ointment is effective for facial and intertriginous psoriasis. Journal of the American Academy of Dermatology 2004; 51.
19. Meingassner J G, Aschauer H, Stuetz A, Billich A. Pimecrolimus permeates less than tacrolimus through normal, inflamed, or corticosteroid-pretreated skin. Experimental Dermatology 2005; 14.
20. Merck Index—an encyclopaedia of chemicals, drugs and biologicals. Whitehouse Station, N.J., USA: Merck Research Laboratories, Division of Merck & Co., INC., 2001.
21. Pillai R, Schmaus G, Lange S, Roeding J. 1,2-Pentanediol—a multifunctional ingredient for personal care applications. SOFW Journal 2005; 131.
22. Remitz A, Reitamo S, Erkko P, Granlund H, Lauerma A I. Tacrolimus ointment improves psoriasis in a microplaque assay. British Journal of Dermatology 1999; 141.
23. Ruzicka T, Bieber T, Schopf E, et al. A short-term trial of tacrolimus ointment for atopic dermatitis. New England Journal of Medicine 1997; 337.
24. SciFinderScholar. Advanced Chemistry Development (ACD/Labs) Software V8.14 for Solaris™ 2007.
25. Singalavanija S, Noppakun N, Limpongsanuruk W, et al. Efficacy and safety of tacrolimus ointment in pediatric Patients with moderate to severe atopic dermatitis. Journal of the Medical Association of Thailand=Chotmaihet thangphaet 2006; 89.
26. Steele J A, Choi C, Kwong P C. Topical tacrolimus in the treatment of inverse psoriasis in children. Journal of the American Academy of Dermatology 2005; 53.
27. Wohlrab J. Der Einfluss von L-Arginin auf die Regulation der epidermalen Arginase/:Aachen:Shaker, L2-http://worldcatorg/ocic/50052467, 2001.
28. Yamamoto T, Nishioka K. Topical tacrolimus is effective for facial lesions of psoriasis. Acta Dermato-Venereologica 2000; 80.
29. Yamamoto T, Nishioka K. Successful treatment with topical tacrolimus for oral psoriasis. Journal of the European Academy of Dermatology and Venereology 2006; 20.
30. Zonneveld I M, Rubins A, Jablonska S, et al. Topical tacrolimus is not effective in chronic plaque psoriasis—A pilot study. Archives of Dermatology 1998; 134.

The invention claimed is:
1. A pharmaceutical composition comprising:
a therapeutically active ingredient selected from the group consisting of sirolimus, everolimus, tacrolimus, pimecrolimus, ridaforolimus, temsirolimus, and zotarolimus,
a hydrophilic component;
a lipophilic component; and
an amphiphilic component,
wherein the composition is formulated as a microemulsion; and
wherein the hydrophilic component comprises a combination of water and a liquid glycol which is preferably selected from glycerol, propylene glycol, 1,2-pentylene glycol, and polyethylene glycol, further characterized in that the ratio of water to the liquid glycol is in the range from about 1:10 to about 10:1.
2. The pharmaceutical composition of claim 1, comprising tacrolimus, or a salt or derivative thereof, wherein essentially all of the tacrolimus is in solubilised form.
3. The pharmaceutical composition of claim 1, wherein the microemulsion is in liquid form.
4. The pharmaceutical composition of claim 1, wherein the hydrophilic component is present at an amount of at least about 20 wt.-%, relative to the weight of the composition.
5. The pharmaceutical composition of claim 1, wherein the weight ratio of the hydrophilic component to the amphiphilic component is 1:1 or higher.
6. The pharmaceutical composition of claim 1, wherein the lipophilic component comprises at least one excipients selected from isopropyl myristate, isopropyl palmitate, dibutyl adipate, diisopropyl adipate, and triglycerides.
7. The pharmaceutical composition of claim 1, wherein the amphiphilic component comprises at least one surfactant selected from phospholipids, alkyl polyglucosides, sorbitan esters with fatty acids, polyalkyleneglycol ethers of fatty alcohols, and pegylated mono- and diesters of glycerol with fatty acids.
8. The pharmaceutical composition of claim 1, wherein the amphiphilic component comprises at least two surfactants.
9. The pharmaceutical composition of claim 2, wherein
the hydrophilic component comprises a combination of water and propylene glycol or pentylene glycol;
the lipophilic component is selected from dibutyl adipate and isopropylmyristate;
the amphiphilic component comprises a lecithin combined with an alkyl polyglucoside, or a lecithin combined with sorbitan monooleate, or a lecithin combined with polyoxyethyleneglycol monostearate.
10. The pharmaceutical composition of claim 9, wherein the ratio of water to propylene glycol or pentylene glycol is in the range of about 3:1 to 1:3.
11. The pharmaceutical composition of claim 9, wherein the hydrophilic component comprises at least 20 wt % of water relative to the total composition.

12. The pharmaceutical composition of claim 1, wherein the composition is formulated for topical use in the prophylaxis and/or treatment of atopic dermatitis, psoriasis, or collagenosis.

* * * * *